(12) United States Patent
Michael

(10) Patent No.: US 7,978,861 B2
(45) Date of Patent: Jul. 12, 2011

(54) METHOD AND APPARATUS FOR CONTINUOUS NOISE EXPOSURE MONITORING

(75) Inventor: Kevin Michael, State College, PA (US)

(73) Assignee: Sperian Hearing Protection, LLC, San Diego, CA (US)

( * ) Notice: Subject to any disclaimer, the term of this patent is extended or adjusted under 35 U.S.C. 154(b) by 1729 days.

(21) Appl. No.: 11/130,267

(22) Filed: May 17, 2005

(65) Prior Publication Data

US 2005/0254667 A1   Nov. 17, 2005

Related U.S. Application Data

(60) Provisional application No. 60/571,511, filed on May 17, 2004.

(51) Int. Cl.
H04R 29/00 (2006.01)
A61F 11/06 (2006.01)
H04R 25/00 (2006.01)

(52) U.S. Cl. ............ 381/60; 381/72; 381/312; 381/315; 381/317; 381/318

(58) Field of Classification Search ............... 381/72, 381/71.6, 328, 57, 58, 71.8, 60, 312, 317, 381/74, 315; 128/864, 867
See application file for complete search history.

(56) References Cited

U.S. PATENT DOCUMENTS

| 5,757,930 A | 5/1998 | Seidemann |
| 6,456,199 B1 | 9/2002 | Michael |
| 7,006,647 B1 * | 2/2006 | Wuersch ............ 381/324 |
| 2001/0050993 A1 * | 12/2001 | Douglas ............ 381/71.6 |
| 2002/0080979 A1 * | 6/2002 | Brimhall et al. ............ 381/72 |
| 2005/0232453 A1 * | 10/2005 | Fideler ............ 381/322 |

* cited by examiner

Primary Examiner — Vivian Chin
Assistant Examiner — George Monikang
(74) Attorney, Agent, or Firm — Conley Rose, P.C.; Kristin Jordan Harkins

(57) ABSTRACT

A method for continuously monitoring noise exposure level of a person via measuring sound level within an ear canal of the person using a sound measurement means linked to a sound level recording device external to the ear canal, wherein the sound measurement means may be shielded from the environment by a hearing protective device, and wherein the cable does not interfere with the ability of the hearing protective device to reduce noise exposure level in the ear canal. Also provided are a system comprising a sound measurement means mounted within an ear canal of the person, an external sound level recording means and a linking cable. Further provided is a system for providing continuous noise exposure monitoring level of a person, and for providing radio communication in a noisy environment, said system comprising the above sound monitoring system linked to a radio signal transmission means, and is switchable between said sound level recording means in a recording mode and said radio signal transmission means in a communication mode.

17 Claims, 3 Drawing Sheets

METHOD AND APPARATUS FOR CONTINUOUS NOISE EXPOSURE MONITORING

CROSS REFERENCE FOR RELATED APPLICATIONS

This application claims the priority of U.S. Provisional Application No. 60/571,511, filed May 17, 2005, the disclosure of which is expressly incorporated by reference herein.

BACKGROUND OF THE INVENTION

Long-term exposure to high levels of noise may cause hearing loss and other health hazards, and as a consequence U.S. law requires that the exposure level to noise by an individual in a work place be accurately measured and limited. See e.g. 29 C.F.R. §1910.95, and U.S. Pat. No. 6,456,199 for a general discussion. Noise dosimeter is commonly used in the industry to measure the cumulative noise exposure by an individual over the course of a full work shift, and the effectiveness of hearing protection devices (HPD) or noise control devices.

U.S. Pat. No. 6,456,199, incorporated herein by reference, discloses a cost-effective and unobtrusive means of continuously monitoring an individual's actual noise exposure rather than simply measuring either hearing protector attenuation or unprotected individual exposure.

The monitoring system includes at least one microphone, housed in the interior of a hearing protective device. Exposure dosage calculation includes periods when the HPD is worn (primary microphone position) and periods when it is not worn (secondary microphone position). When the HPD is worn at the primary position, it measures the noise level with the protective device in effect, and when the HPD is worn at the secondary position, it measures the noise level of the environment without the protective device. This provides an accurate measurement of the actual exposure dosage because invariably workers have their hearing protectors donned for part of the day and removed for the rest part of the day.

Methods of measuring noise dose or sound level incident upon the worker's ear canal ("in-the-ear-canal sound level measurements") are known in the prior art, but are performed with a probe tube microphone. These devices are not suitable for measuring under hearing protectors. First, the tube breaks the seal of the protector, thus compromising the protection. Second, the tube is acoustically transparent at some frequencies, making the system inappropriate for use in high noise areas. For example, U.S. Pat. No. 5,757,930 to Seidemann, describes a system of noise measurement interior to an insert-type hearing protector. This system consists of a microphone mounted at the interior tip of a modified earplug, not mounted in the ear canal. The Seidemann system is designed to measure hearing protector attenuation, not personal noise exposure Once the earplug is removed (unprotected condition), it no longer measures the noise exposure level in the ear canal. Furthermore, the Seidemann system is not usable with muff-type HPDs.

DESCRIPTION OF THE INVENTION

The present invention discloses an alternative to the methodology of U.S. Pat. No. 6,456,199, and associated devices useful therefore. According to one embodiment of the present invention, a miniature microphone is mounted in the worker's ear canal for the entire duration of the work shift, and noise level incident to the ear canal is constantly measured. Using this technique, the measurement accurately reflects the actual noise exposure level at the worker's ears.

According to the present invention, the microphone stays in one position, accurately measuring exposure under both protected and unprotected conditions. An advantage of the present invention is that conventional hearing protection devices, such as ear muffs or ear plugs, can be used by the workers, without interfering with the accurate measurement of the actual exposure levels of the workers. In the unprotected condition (i.e., an HPD is not worn), the ear canal microphone accurately measures the sound pressure that is incident on the ear canal. In the protected condition, the canal-mounted microphone measures the sound pressure that is present interior to the hearing protection.

One key advantage of the present invention is that the measurement microphone stays constantly in one position within the worker's ear canal, thereby providing the most accurate measurement of "center-of-head" (COH) noise exposure, the definitive metric used by the United States Occupational Safety and Health Administration (OSHA) and Mining Safety and Health Administration (MSHA) to determine noise regulation compliance. Laboratory comparison measurements have verified that the "in-the-ear-canal" sound level or noise dose measurements of the present invention accurately reflect the COH equivalent. All damage risk criteria in the US have been developed using the COH with the worker absent as the default measurement location.

Another advantage of the present invention is that it is compatible with commercially available hearing protective devices and existing communication systems.

Figure 1:
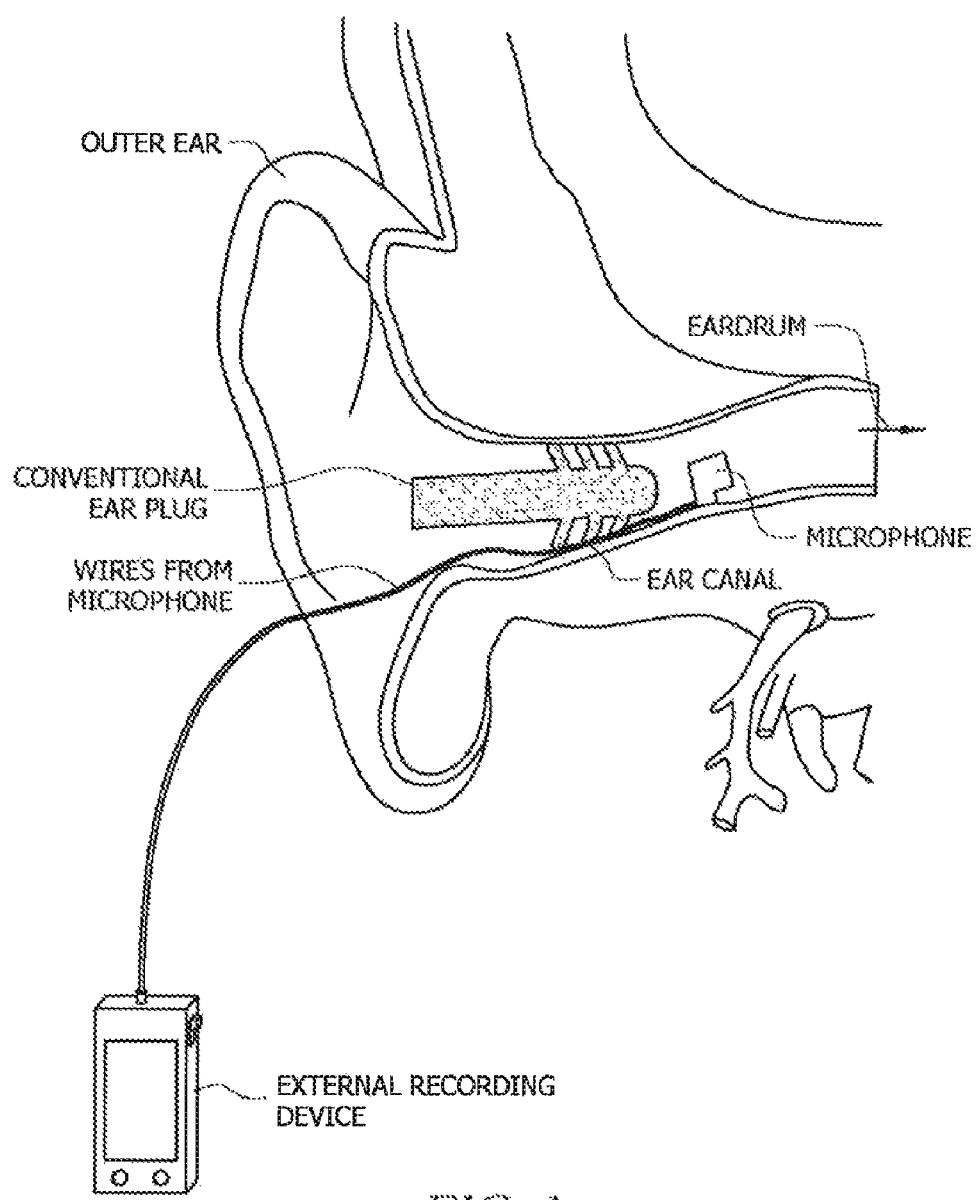
FIG. 1 illustrates an embodiment of the apparatus for continuous noise exposure monitoring in which a microphone is mounted in the user's ear canal, such that a conventional earplug may be inserted into the user's ear to seal the ear canal, with the microphone sealed inside the ear canal.
Figure 2:
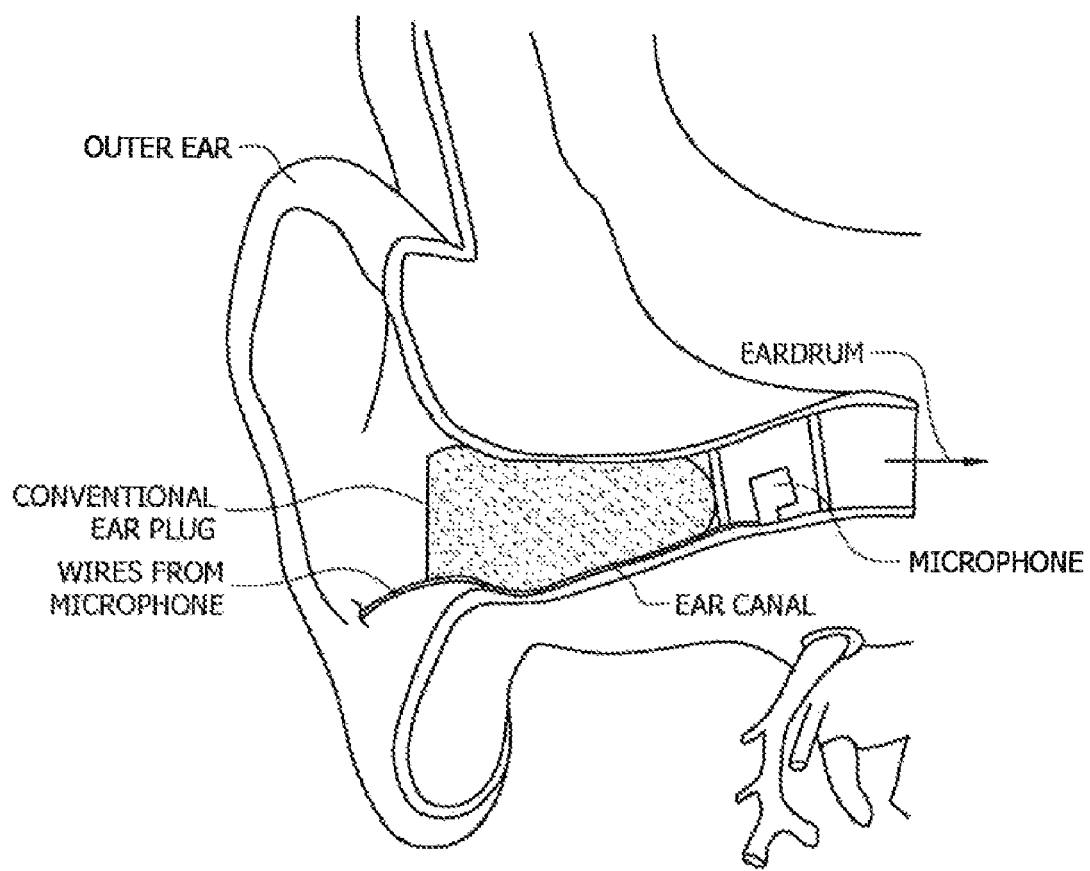
FIG. 2 illustrates an embodiment in which the microphone is enclosed within a sound-transparent cage that is mounted in the user's ear canal, such that a conventional earplug may be inserted into the user's ear to seal the ear canal without occluding the microphone.

Microphones suitable for the present invention should be constructed or position in such a way that an insert-type earplug cannot be inserted over the microphone. Occlusion by the earplug inside the ear canal will render the measurements inaccurate (see FIG. 1). One approach to accomplish this objective is using a small, sound-transparent cage to enclose the microphone (see e.g. FIG. 2).

The measurement microphone is generally linked via cables or wires to an electrical signal modulating and/or recording device, to record and calculate the sound level. According to the present invention, the wires or cables extending from the microphones to the external circuitry should not cause a breach of the sound barrier of the HPD.

Figure 3:
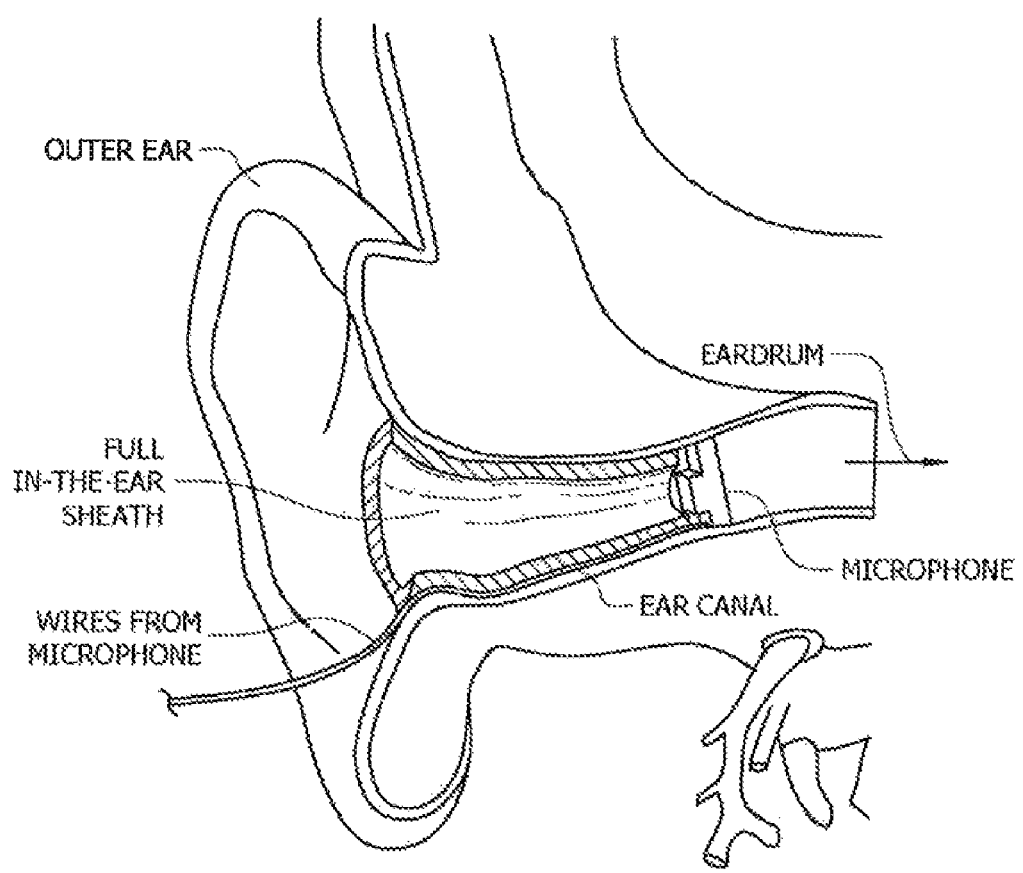
FIG. 3 illustrates an embodiment comprising a microphone and an in-the-ear sheath inserted into the user's ear canal, with the wire from the microphone being embedded in the sheath so that the wire would not interfere with the seal formed by a conventional earplug.

Thus, the cables or wires should be thin, e.g. preferably, 36 AWG or smaller, so that an effective seal can be made with the plug against the canal walls. Alternatively, the wires extending from the microphone to the external components can be embedded in a shell-like device that conforms to the ear canal walls, see for example FIG. 3.

This thin, shell-like device, or in-the-ear (ITE) sheath, is preferably constructed of a hypo-allergenic silicone material, and would be designed to accept insert-type hearing protectors. In preferred embodiments, the present invention provides a range of ITE sheath sizes to fit most ear canal sizes and geometries. The ITE sheath device may also be customized to fit a particular individual user's ears, if desired.

While this ITE device is designed to be flexible to conform to the ear canal walls, it is also stiff enough to remain open to ensure that sound can reach the measurement microphone.

One further advantage of the instant method is that it well-suited for a combined hearing protection and 2-way radio communication system. The radio communication transceiver(s) can be mounted adjacent to the monitoring microphone. The communication speaker introduces an audible signal near the eardrum.

The communication microphone would also be able to pick up and transmit audio signals that are introduced into the ear canal when the worker speaks, but not environmental noise. This is a particularly effective communication system in noisy environments.

I claim:

1. A method for continuously monitoring noise exposure level of a person, comprising:
providing a sound measurement means for measuring sound level, wherein the sound measurement means is operable to be shielded from the environment by a hearing protective device, wherein the sound measurement means is separately mounted within an ear canal of the person apart from the hearing protective device, wherein the sound measurement means is linked via a suitable cable to a sound level recording device external to the ear canal, and wherein the cable does not interfere with the ability of the hearing protective device to reduce noise exposure level in the ear canal; and, further comprising measuring by the sound measurement means noise exposure under both protected and unprotected conditions while the sound measurement means is located in only a single position.

2. A method according to claim 1, wherein the sound measurement means is a microphone.

3. A method according to claim 1, wherein the hearing protective device is an ear plug or an ear muff.

4. A method according to claim 1, wherein the sound measurement means is enclosed in a sound-transparent cage in the ear canal between the hearing protective device and the eardrum.

5. A method according to claim 1, wherein the suitable cable is embedded in a shell which fits snuggly in the ear canal.

6. A method according to claim 5, wherein the shell is made of a hypo-allergenic silicon material.

7. A method according to claim 1, wherein the cable is 36 AWG or smaller so that the cable will not interfere with the hearing protective device's ability to form an effective seal within the ear canal.

8. A method according to claim 4, wherein the sound-transparent cage prevents an insert-type hearing protective device from being inserted over the sound measurement device.

9. A method according to claim 5, wherein the shell allows for insertion of an insert-type hearing protective device.

10. A method according to claim 5, wherein the shell comprises a sheath with an opening, an exterior surface that conforms to the ear canal walls, and an interior surface that accepts an insert-type hearing protective device for optionally sealing the opening and shielding the sound measurement means from the environment.

11. A system for providing continuous noise exposure monitoring level of a person, and for providing radio communication in a noisy environment, said system comprising:
a sound measurement means for measuring sound level, a sound level recording means, a cable linking the sound measurement means and the sound level recording means, a radio transceiver mounted next to the sound measurement means in the ear canal, said radio transceiver is linked to a radio signal receiving means external to the ear canal,
wherein the sound measurement means is mounted within an ear canal of the person, wherein the sound level recording device is external to the ear canal,
wherein said sound measurement means is further linked to a radio signal transmission means, and is switchable between said sound level recording means in a recording mode and said radio signal transmission means in a communication mode,
wherein the sound measurement means is shielded from the environment by a hearing protective device that is separate and apart from the sound measurement means, and wherein the cable does not interfere with the ability of the hearing protective device to reduce noise exposure level in the ear canal,
wherein in a communication mode, the sound measurement means is linked to the radio transmission means and detects and transmits the speech signal in the ear canal from the person, and in the recording mode the sound measurement means records the noise level penetrated from the hearing protective device to the ear canal.

12. A system according to claim 11, wherein the sound measurement means measures exposure under both protected conditions, when shielded by the hearing protective device, and unprotected conditions, without shielding by the hearing protective device, while located in only a single position.

13. A system according to claim 11, wherein the cable is embedded in a shell which fits snuggly in the ear canal, and the shell comprises a sheath with an opening therethrough, an exterior surface that conforms to the ear canal walls, and an interior surface that accepts an insert-type hearing protective device for optionally sealing the opening and shielding the sound measurement means from the environment.

14. A method for continuously monitoring noise exposure level of a person in both protected conditions, when the person is shielded by a separate hearing protective device, and unprotected conditions, without shielding by the hearing protective device, comprising:
providing a sound measurement means for measuring sound level, wherein the sound measurement means is essentially sound transparent and is operable to be shielded from the environment by the separate hearing protective device;
mounting the sound measurement means within an ear canal of the person; and
measuring noise exposure by the sound measurement means.

15. The method of claim 14, wherein the sound measurement means measures exposure under both protected and unprotected conditions while located in only a single position; and wherein the sound measurement means is not attached to the hearing protective device but is distinct and apart from the hearing protective device.

16. The method of claim 14, further comprising:
employing the hearing protective device to shield the ear canal; and
measuring by the sound measurement means protected noise exposure level;
wherein the sound measurement means is linked to a sound level recording device external to the ear canal; and
wherein linking the sound measurement means to the sound level recording device does not interfere with the ability of the hearing protective device to reduce noise exposure in the ear canal.

17. The method of claim 16, further comprising:
removing the hearing protective device; and
measuring by the sound measurement means unprotected noise exposure level.

* * * * *

UNITED STATES PATENT AND TRADEMARK OFFICE
CERTIFICATE OF CORRECTION

PATENT NO. : 7,978,861 B2
APPLICATION NO. : 11/130267
DATED : July 12, 2011
INVENTOR(S) : Kevin Michael Page 1 of 1

It is certified that error appears in the above-identified patent and that said Letters Patent is hereby corrected as shown below:

IN THE SPECIFICATIONS:

Column 1, Line 9, replace "May 17, 2005" with --May 17, 2004--

Signed and Sealed this
Twenty-eighth Day of August, 2012

David J. Kappos
*Director of the United States Patent and Trademark Office*